US011825258B2

(12) United States Patent
Heo et al.

(10) Patent No.: US 11,825,258 B2
(45) Date of Patent: Nov. 21, 2023

(54) HEADSET ASSEMBLY USING BONE CONDUCTION

(71) Applicant: MOBIFREN CO., LTD, Gumi-si (KR)

(72) Inventors: Ju Won Heo, Gumi-si (KR); Kwi Hwan Kim, Seoul (KR)

(73) Assignee: MOBIFREN CO., LTD, Gumi-si (KR)

( * ) Notice: Subject to any disclaimer, the term of this patent is extended or adjusted under 35 U.S.C. 154(b) by 0 days.

(21) Appl. No.: 17/560,526

(22) Filed: Dec. 23, 2021

(65) Prior Publication Data

US 2023/0209236 A1 Jun. 29, 2023

(51) Int. Cl.
*H04R 1/10* (2006.01)
*A61N 1/04* (2006.01)

(52) U.S. Cl.
CPC ......... *H04R 1/1008* (2013.01); *A61N 1/0456* (2013.01); *H04R 1/105* (2013.01)

(58) Field of Classification Search
CPC ..... H04R 1/1008; H04R 1/105; A61N 1/0456
See application file for complete search history.

(56) References Cited

U.S. PATENT DOCUMENTS

| | | | |
|---|---|---|---|
| 10,154,334 B1* | 12/2018 | Lin | H04R 19/04 |
| 2009/0185699 A1* | 7/2009 | Kim | H04R 1/1066 |
| | | | 381/151 |
| 2019/0014425 A1* | 1/2019 | Liao | H04R 9/066 |
| 2019/0075389 A1* | 3/2019 | Jan | A42B 3/306 |
| 2019/0253781 A1* | 8/2019 | Kunimoto | H04R 1/00 |
| 2019/0313184 A1* | 10/2019 | Truhill | A61M 21/02 |
| 2022/0337929 A1* | 10/2022 | Wang | H04R 1/105 |
| 2022/0377451 A1* | 11/2022 | Shi | H04R 1/1075 |

* cited by examiner

*Primary Examiner* — Oyesola C Ojo
(74) *Attorney, Agent, or Firm* — Hauptman Ham, LLP

(57) ABSTRACT

A bone conduction-using headset: a pair of main bodies (200), a pair of unit bodies (220); a pair of suspenders (210), each of the suspenders having a shape of letter "U";
and a connector (240) connected to the main bodies (200) wherein: each of the main bodies extends downward at a rear side R of the ear E of the user P, has a length longer in a longitudinal direction thereof than in a transverse direction thereof; the connector (240) is connected to and extends from ends of the main bodies (200) toward a rear side of a neck N of the user P at a wearing inclination angle a with respect to a longitudinal axis C of the main body (200); and an inner circumference part R of the connector (240) is located around the rear side of the neck N of the user P.

1 Claim, 10 Drawing Sheets

HEADSET ASSEMBLY USING BONE CONDUCTION

BACKGROUND OF THE INVENTION

1. Field of the invention

The present disclosure relates to a headset assembly using bone conduction and, more particularly, to an improvement in the structure of a headset for application of bone conduction suitable to be employed in applied products for selectively or simultaneously transferring a sound signal and an electric signal for mental therapy to the human auditory nerve according to a bone conduction method.

2. Description of the Prior Art

Recently, in addition to sound listening through sound propagation to the human eardrum caused by vibration of air, the technology of bone conduction to enable sound listening has been widely adopted. The technology of bone conduction is a technology using the physical property (i.e., the vibration conductivity) of a skull to transfer sound to the cochlea and then to the brain through the auditory nerve.

A headset using the technology of bone conduction can prevent the occurrence of an accident, which may occur in an environment where a user wearing a conventional air-conduction headset is unable to hear any sound from the surroundings, and can prevent noise-induced deafness caused by a conventional air-conduction headset. Therefore, the bone conduction headset is advantageous for users' health and is thus being increasingly spread.

A headset using the technology of bone conduction includes a bone conduction unit as a means for generating mechanical vibration for transferring sound or a sound signal to the human auditory nerve. The bone conduction unit transforms an electric signal of input sound into mechanical vibration and outputs the mechanical vibration, so that the mechanical vibration is conducted through the skin and bone of the human skull. Usually, the bone conduction unit includes a frame, a voice coil, a magnet, and a vibration plate.

The vibration plate of the bone conduction unit should be brought into tight contact with the skin of the human skull, differently from a conventional speaker-type headset which can transfer sound even when there is a clearance to some degree between the headset and the human skin.

Additionally, a headset assembly may be configured to include a bone conduction unit having a conductive vibration plate serving as a conductive electrode or a separate electrode member together with a bone conduction unit having a non-conductive vibration plate, so that the headset assembly can be used not only for listening to music in normal times but also for a special therapy by application of electric stimulus through the electrode when necessary.

A technology so-called transcutaneous electrical nerve stimulation (TENS) is conventionally known as a technology for applying a controlled electric signal to the human body. According to TENS, calculated electric stimulus is applied to a human body to relieve pain. Therefore, TENS is known as having various effects and is being actively studied in various countries.

It is known that a human body shows a good response to a specific frequency, and devices using TENS can exhibit various effects by providing a percutaneous energy through vibration to electrodes arranged on multiple parts of a human body. Further, TENS is usually used for relieving pain through application of electric stimulus to the skin.

TENS uses several types of electric waves characterized by frequencies, pulse widths, and amplitudes, for treatment by application of the waves through external surface electrodes. Therefore, TENS is non-medicinal, non-invasive, and non-toxic, and thus has nearly no reasons for prohibition thereof. Academically approved effects of the TENS therapy include alleviating depression, improvement of sleep quality, stress relief, concentration enhancement, and improvement of body mechanisms.

A treatment device (named a "transcranial electric stimulus therapy device") including a chair for seating a patient thereon and a head-worn band for applying electric stimulus to a human body has been widely spread in hospitals in the Republic of Korea and has exhibited a good effect in alleviating depression. However, this chair type treatment device is very expensive and is not portable, thus necessitating a user who wants to use the device to visit the place where the device is installed.

Therefore, there has been a demand for a distributed type low-priced device having a simple structure, which can treat various types depression patients, enhance concentration of hard workers including examinees, treat children with TIC disorders, treat people with ADH, etc.

In the bone conduction device, the electrode for TENS therapy is configured by either a separate electrode member or the vibration plate of the bone conduction unit for sound generation, which is made from a conductive metal, the electrode is connected to a wire for transferring an electric signal for control, and a control unit controls generation and transfer of either one of or both of a sound signal and an electric signal for TENS therapy to enable a user to perform either one of or both of actions of music listening and TENS therapy.

That is, the bone conduction device provides a selectable TENS therapy function in addition to a general headset function for music listening, etc.

SUMMARY OF THE INVENTION

In order to enable a conduction-applied headset to exhibit optimum functions, it is important to bring the vibration plates of the bone conduction units into tight contact with skin behind both ears of a wearer's head. To enable such tight contact, the bone conduction units are made separately from and are connected to the headset body through suspenders, which are elastic band-shaped earring members. The elasticity of the suspenders enables the bone conduction units to be in tight contact with the skin of the wearer's head.

The sizes of human head circumferences have a wide variety of deviation according to the genetic, growth, and environmental factors. Therefore, in the case of using a headset including a head band of a fixed inner diameter, the inner circumference part of the head band may be spaced a gap from some wearers' heads due to the differences in the size of the head circumferences.

In order to solve such a problem, the headset may employ a separate member for length adjustment of the head band. However, such a separately employed member may not only increase the manufacturing cost but may also apply a sense of pressure to a user's head or cause unpleasant feeling to the user when the user leans against a headrest, etc. for long time in order to listen to music, etc.

The present disclosure has been made in order to solve the above-mentioned problems in the prior art, and an aspect of the present disclosure is to provide a conduction-applied headset assembly which does not require a separate mechanical structure for adjustment of the length of a head band, has a very simple structure, and does not apply a mechanical pressure onto a user's head.

Another aspect of the present disclosure is to provide a conduction-applied headset assembly which allows users having various head circumference sizes and shapes to use the assembly and does not require an additional mechanical configuration for adjustment of the length of a head band for connecting units of both sides of the headset assembly.

In accordance with an aspect of the present disclosure, a headset assembly using bone conduction for conducting a sound signal to a human body through mechanical vibration includes: a pair of main bodies, each of which includes a reception box for receiving an electric member; a pair of unit bodies separated and spaced from the main bodies, each of the unit bodies including a reception box that contains a bone conduction unit; a pair of suspenders for electrically and mechanically connecting the main bodies and the unit bodies, respectively, each of the suspenders being held and suspended on an ear of a user P and having a shape of letter "U"; and a connector connected to the main bodies to be worn on a head of the user, wherein: each of the main bodies extends downward at a rear side of the ear of the user, has a length longer in a longitudinal direction thereof than in a transverse direction thereof, the connector is connected to and extends from ends of the main bodies toward a rear side of a neck of the user at a wearing inclination angle a with respect to a longitudinal axis of the main body; and an inner circumference part of the connector is located around the rear side of the neck of the user when the headset assembly is worn on the user.

In accordance with another aspect of the present disclosure, a headset assembly using bone conduction for conducting a sound signal to a human body through mechanical vibration includes: a pair of main bodies, each of which includes a reception box for receiving an electric member; a pair of unit bodies separated and spaced from the main bodies, each of the unit bodies including a reception box that contains a bone conduction unit; a pair of suspenders for electrically and mechanically connecting the main bodies and the unit bodies, respectively, each of the suspenders being held and suspended on an ear E of a user P and having a shape of letter "U"; and a connector connected to the main bodies to be worn on a head of the user, wherein: each of the main bodies extends downward at a rear side R of the ear E of the user P, has a length longer in a longitudinal direction thereof than in a transverse direction thereof; the connector is connected to and extends from ends of the main bodies toward a rear side of a neck of the user at a wearing inclination angle a with respect to a longitudinal axis of the main body, so that an inner circumference part of the connector is located around the rear side of the neck of the user when the headset assembly is worn on the user; and the bone conduction unit in each of the unit bodies includes a vibration plate unit and an electrode member, and an electric signal for transcutaneous electrical nerve stimulation (TENS) is applied from a control device, so as to enable a user to perform sound listening and TENS treatment simultaneously or selectively.

A headset assembly using bone conduction according to the present disclosure employs a connector, which is a single band having an improved configuration and mechanical characteristics, so as to enable most users to use the headset assembly using bone conduction, thereby making it unnecessary to replace the band. Therefore, the present disclosure can remarkably reduce the manufacturing cost.

In addition, the present disclosure provides a headset assembly using bone conduction which can be easily used by users having abnormal head shapes or circumferences or women having long and voluminous hair.

Moreover, the present disclosure provides a headset assembly using bone conduction which can be properly used for TENS therapy as well as for sound listening.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Hereinafter, various exemplary embodiments of specific exemplary embodiments will be described in detail hereinbelow with reference to the drawings.

Figure 1:
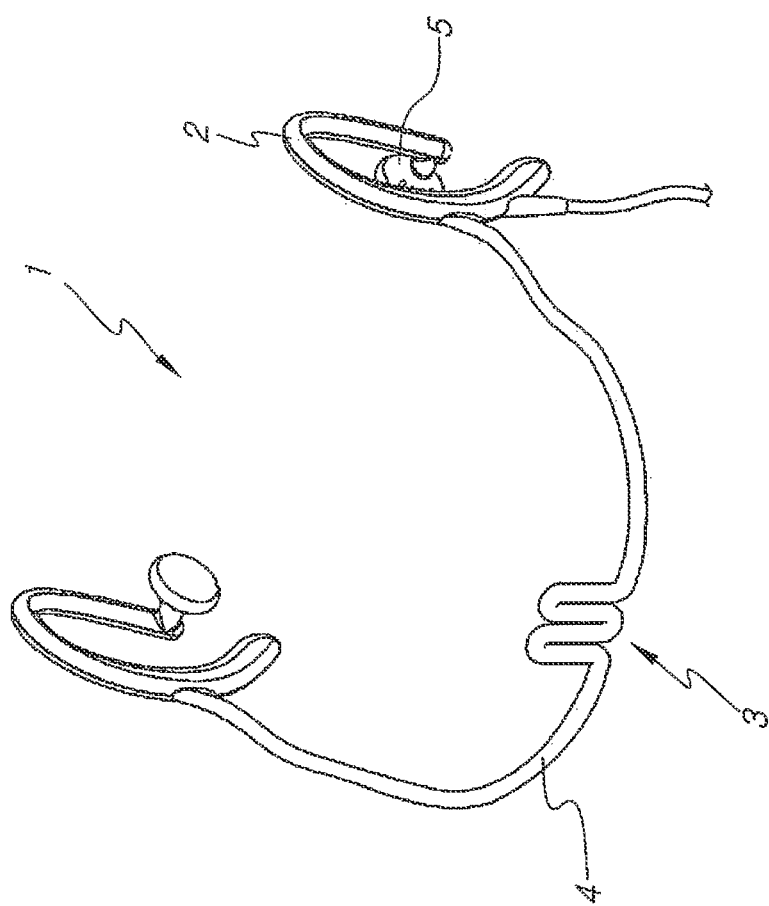
FIG. 1 is a perspective view illustrating the structure of a headband of a headset according to a prior art.
Figure 2:
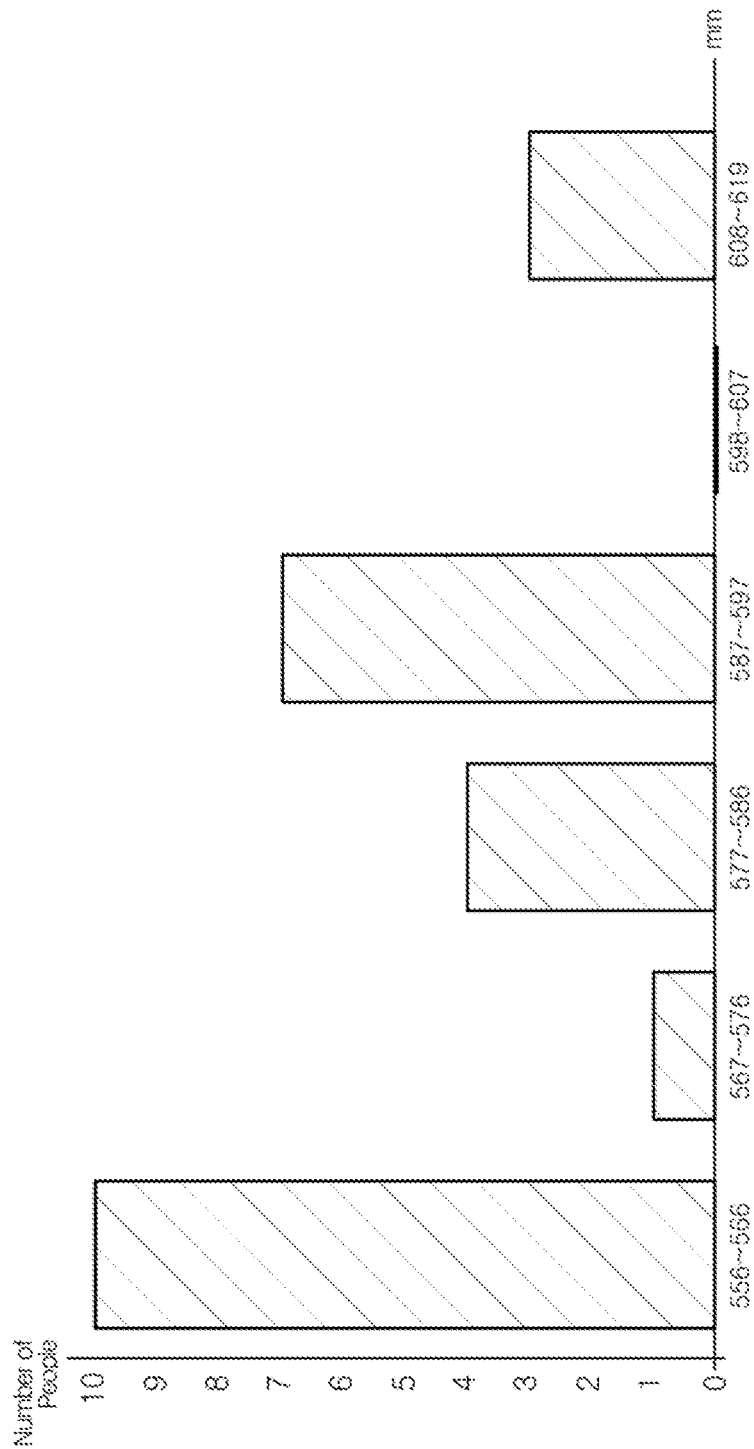
FIG. 2 is a table showing statistical distribution data of head circumferences of Koreans for describing the technical idea of a headset assembly using bone conduction according to the present disclosure.
Figure 3:
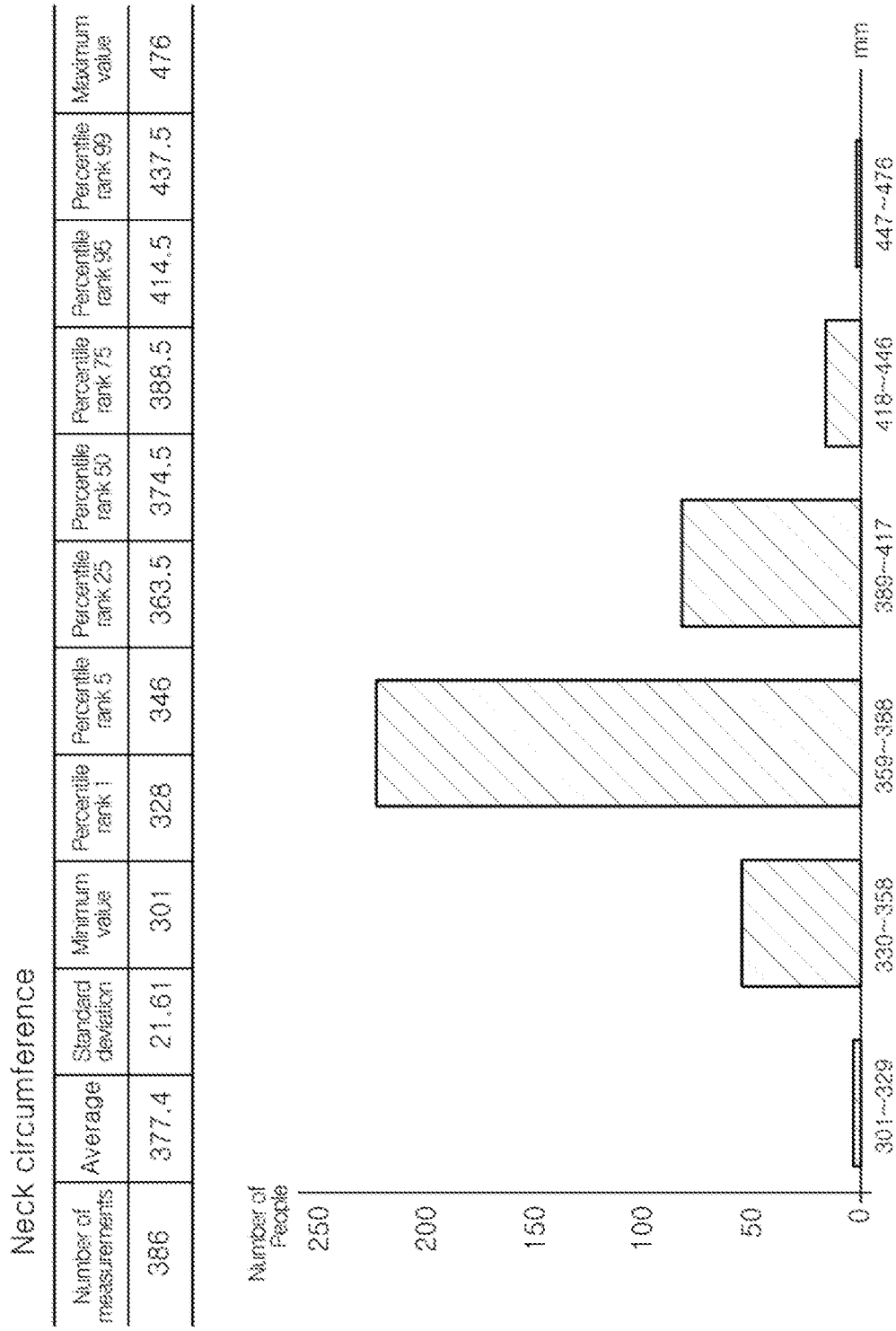
FIG. 3 is another table showing statistical distribution data of head circumferences of Koreans for describing the technical idea of a headset assembly using bone conduction according to the present disclosure.
Figure 4:
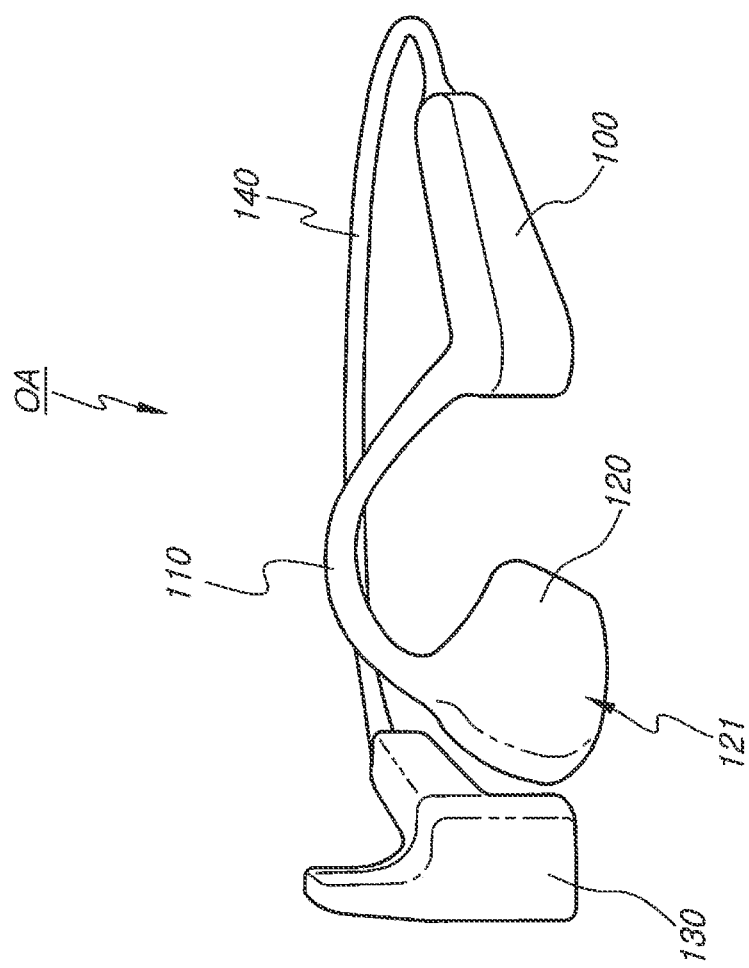
FIG. 4 is a perspective view illustrating an exemplary conventional headset product to which the technical idea of a headset assembly using bone conduction according to the present disclosure can be properly applied.
Figure 5:
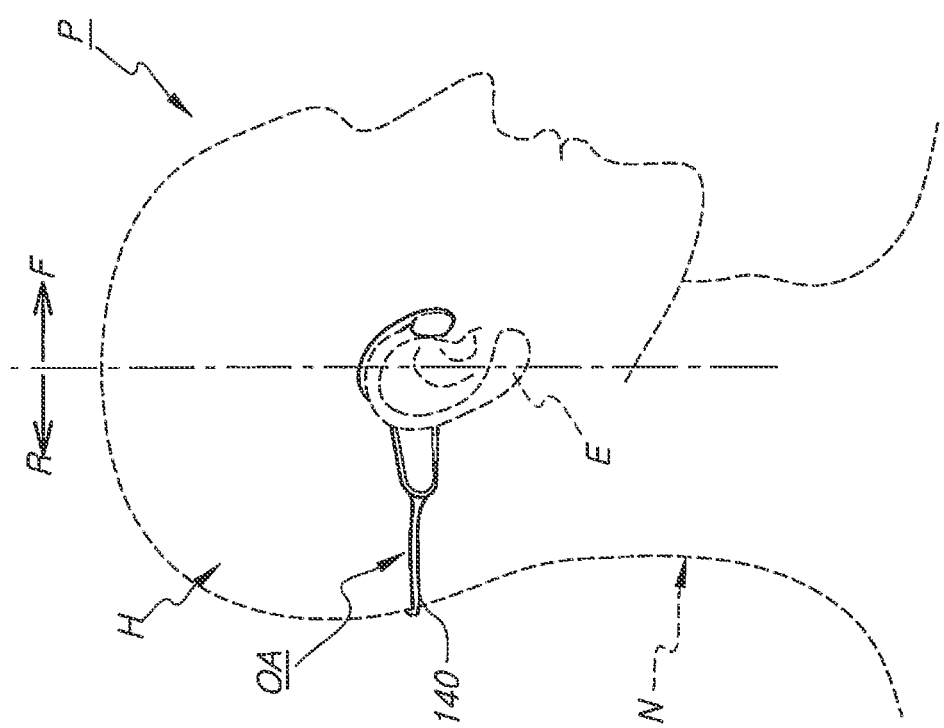
FIG. 5 is a side view for describing the structure and problems of a conventional headset product in a worn state.
Figure 6:
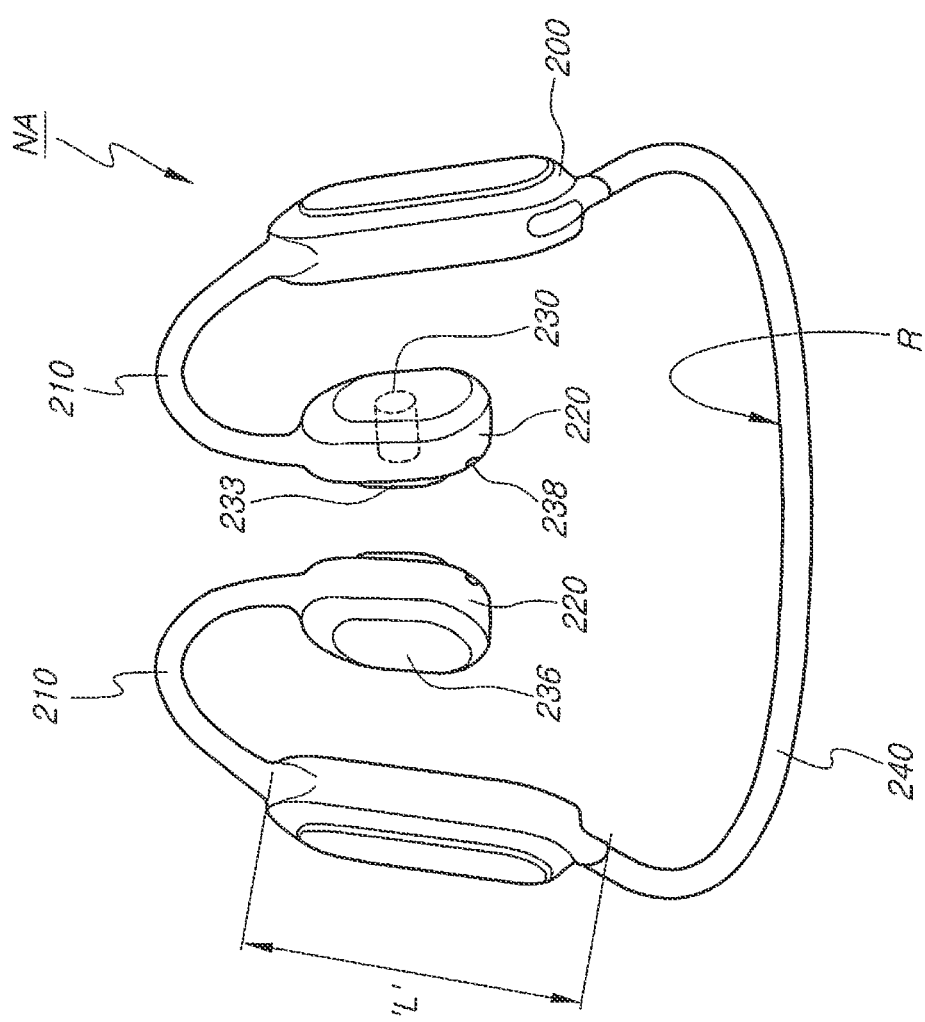
FIG. 6 is a front perspective view of a headset assembly using bone conduction according to the present disclosure.
Figure 7:
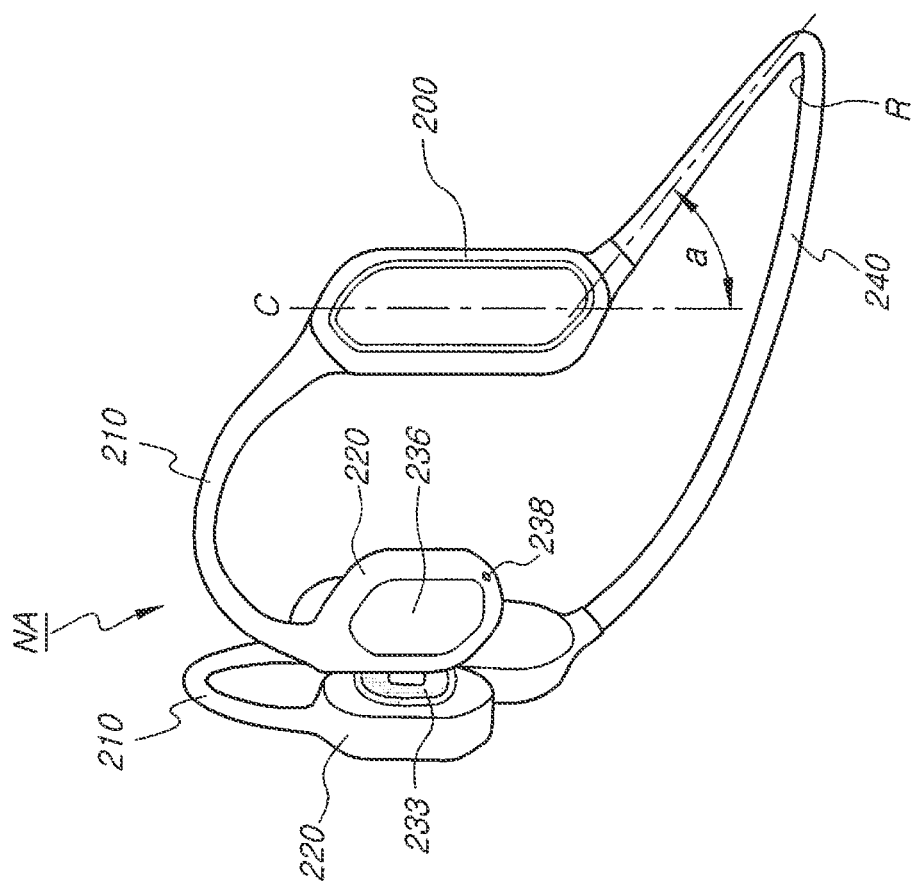
FIG. 7 is a side elevational perspective view of a headset assembly using bone conduction according to the present disclosure.
Figure 8:
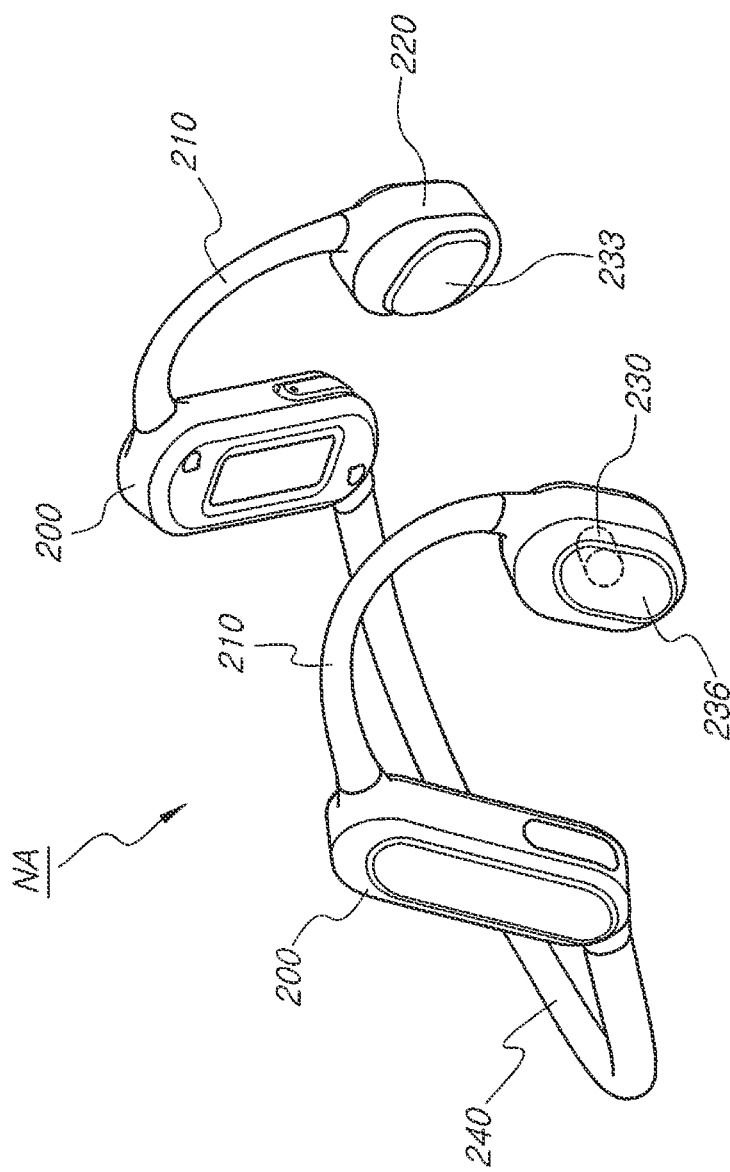
FIG. 8 is another side elevational perspective view of a headset assembly using bone conduction according to the present disclosure.
Figure 9:
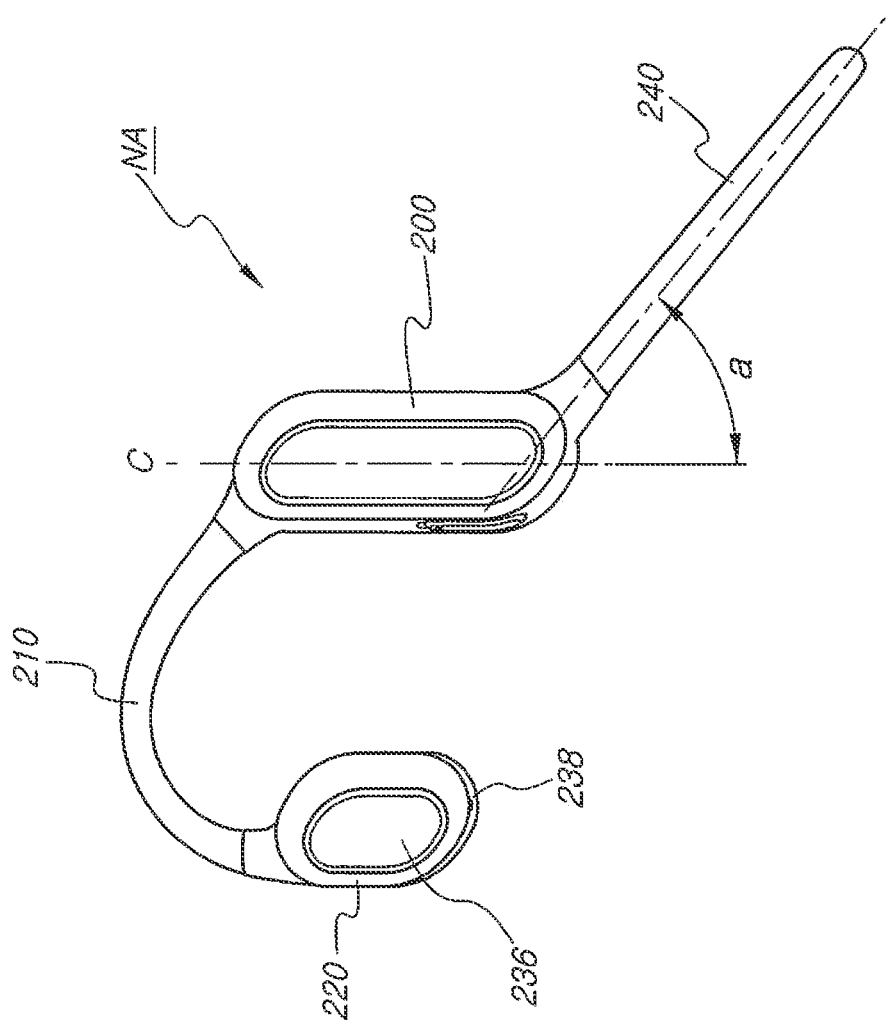
FIG. 9 is a right side view of a headset assembly using bone conduction according to the present disclosure.
Figure 10:
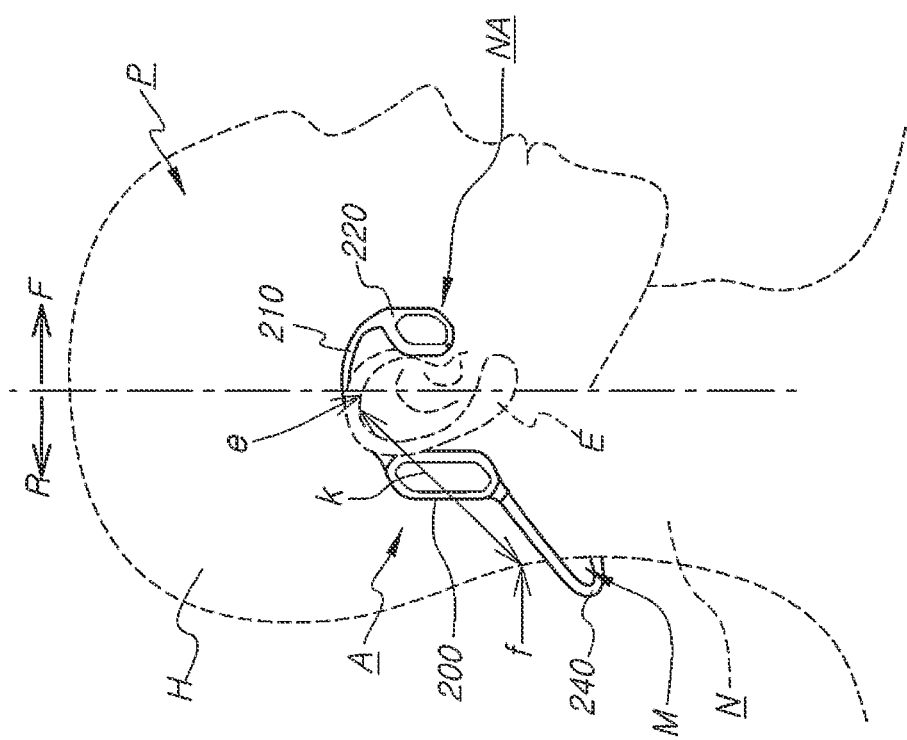
FIG. 10 is a view showing a state in which a headset assembly using bone conduction according to the present disclosure is worn on a user's head.

FIG. 1 is a perspective view illustrating the structure of a headband of a headset according to a prior art, FIG. 2 is a table showing statistical distribution data of head circumferences of Koreans for describing the technical idea of a headset assembly using bone conduction according to the present disclosure, FIG. 3 is another table showing statistical distribution data of head circumferences of Koreans for describing the technical idea of a headset assembly using bone conduction according to the present disclosure, FIG. 4 is a perspective view illustrating an exemplary conventional headset product to which the technical idea of a headset assembly using bone conduction according to the present disclosure can be properly applied, FIG. 5 is a side view for describing the structure and problems of a conventional headset product in a worn state, FIG. 6 is a front perspective view of a headset assembly using bone conduction according to the present disclosure, FIG. 7 is a side elevational perspective view of a headset assembly using bone conduction according to the present disclosure, FIG. 8 is another side elevational perspective view of a headset assembly using bone conduction according to the present disclosure, FIG. 9 is a right side view of a headset assembly using bone conduction according to the present disclosure, FIG. 10 is a view showing a state in which a headset assembly using bone conduction according to the present disclosure is worn on a user's head.

Those figures are sequentially described hereinafter.

Now, a headset assembly using bone conduction according to the present disclosure will be described in detail in comparison with a product of the prior art.

Various types of bone conduction-applied headset assemblies are being circulated in the market, and most headset assemblies have similar external appearances and similar mechanical structures, like a product as shown in FIGS. 4 and 5.

As shown in FIG. 4, a conventional headset OA has a structure, the left side and the right side of which are symmetrical to each other and will be mixedly described below.

In general, the conventional headset includes a pair of main bodies 100 to be placed on a user's head H. Each of the main bodies may be made from synthetic resin and have various box shapes capable of receiving electric members, such as a printed circuit board (PCB) and a battery.

As shown, a suspender 110 is provided at the upper end of each main body 100, is substantially shaped like letter "U", and has a tubular body made from elastic synthetic resin. The suspender 110 is held and suspended on user's ear when the headset is worn on the user. Within the tubular body of the suspender 110, an electric wire (not shown) for electric wiring is disposed.

A unit body 120 is integrally formed with or separately fixed to the front end (corresponding to the face-side F of the head H of the user) of the suspender 110. The unit body has a substantially box shape and contains a bone conduction unit 130 for applying mechanical vibration to the user's head.

The bone conduction unit 130 received in the unit body 120 has vibration plate or vibration plate unit (not shown), which is exposed from the bone conduction unit or is coated with a separate protection plate. The bone conduction unit may further include an embedded microphone and a communication hole (not shown) for a phone call.

Usually, a main button 121 for controlling the headset OA is provided as a touch button on a side opposite to the exposed side of the unit body 120. The main button 121 is provided on the main body 100 in some products.

In the prior art as described above, the main body 100 and the unit body 120 are configured separately and to be connected to each other through the suspender 110. As a result, the suspender 110, which is a tubular body, elastically pushes the vibration plate unit 131 of the bone conduction unit 130 toward the head H of the user to enable a tight contact therebetween. Therefore, most bone conduction-applied headset assemblies being circulated in the market employ the above-described structure.

A pair of assemblies, each including the connection of "the main body 100 - the suspender 110 - the unit body 130", are connected from the left side and the right side through a band type connector 140 or a U-shaped band connected or fixed to the rear ends of the main bodies 100.

In general, it is known that there are big differences in the circumference sizes and shapes of peoples' heads.

Therefore, the conventional headset is disadvantageous in that only the substantially U-shaped connector 140 having a single inner diameter is not enough to overcome the differences and satisfy all users.

The conventional bone conduction-applied headset OA includes, as the connector 140, an elastic band having a single inner diameter and worn around a user's head.

However, for adaptive application to various circumference sizes and shapes H and H' of users' heads, the headset assembly is made to have a size slightly larger than a standard head circumference size of normal users P. Therefore, the connector 140 may pressurize or give pain to the user's head if the connector has been tightened too much. Also, when a user leans his or her head on a headrest or, the suspender 110 may be released from the ear E of the user P if the connector 140 has been loosened to have an excessive length.

Further, in the case of a head H having an abnormal shape due to genetic or growth environmental factors, it may be impossible to wear the headset assembly if the abnormality is out of the allowance range for the deviation in the head circumference size. Moreover, it may be also impossible for a woman having voluminous hair to wear the headset assembly.

In order to solve the above-mentioned problems of the prior art, a headset assembly using bone conduction according to the present disclosure has, through modification of mechanical structure and design, a structure which is not only optimized for listening of music but also enables the assembly to function as a therapy device using TENS.

Hereinafter, a basic technical idea of a headset assembly using bone conduction according to the present disclosure will be described.

It is necessary to determine lengths and shapes of a connector specifically optimized for users, in a statistical viewpoint.

FIG. 2 shows statistical distribution data of head circumferences of Korean individuals of ages ranging from 20 to 29. It is noted from FIG. 2 that the measured values are irregularly scattered over the percentile ranks of the measured values and there are big differences between the percentile ranks. FIG. 3 shows distribution of neck circumferences of individuals, and it is noted from FIG. 3 that the measured values are concentrated on percentile rank 5 of the data with very small deviations.

These data described above prove that the sizes of human neck circumferences fall within a relatively narrow limited range differently from the sizes of human head circumferences.

Therefore, without providing the connector 140 based on the circumference size of a head H of a user P, a headset assembly using bone conduction according to the present disclosure employs a geometric configuration based on the circumference sizes of human necks and includes a connector 240 having a single size (length), which can satisfy various users and requires minimum options for the connector. The connector 240 can be easily placed and worn around a neck N of a user P.

Hereinafter, a bone conduction-using headset assembly NA according to the present disclosure will be described with reference to FIGS. 6 to 10. As noted from the drawings, the left side and the right side of the headset assembly NA are symmetrical to each other and will be mixedly described below.

A bone conduction-using headset assembly NA according to the present disclosure also includes a pair of main bodies 200 to be placed on the head H of a user P, and each of the main bodies may be made from synthetic resin and have various box shapes capable of receiving electric members, such as a printed circuit board (PCB) and a battery.

Also, a suspender 210 is provided at the upper end of each main body 200, is substantially shaped like letter "U", has a tubular body made from elastic synthetic resin, and is to be held and suspended on ears E of the user P.

A unit body 220 is connected to the front end (corresponding to the face-side F of the head H of the user) of the suspender 210, has a substantially box shape, and contains a bone conduction unit 230 for applying mechanical vibration to the user's head. A vibration plate unit 233 is exposed out of the bone conduction unit 230. In the figures, reference numeral 236 indicates a main button for a control function and reference numeral 238 indicates an opening for phone communication.

Referring to FIGS. 6 to 9, the main body 200 of a bone conduction-using headset assembly NA according to the present disclosure is shaped like an elongated box, the length L of which is relatively longer in the longitudinal axis C extending downward at the rear side of an ear E of a user P when the assembly is worn on the user. The elongated box may have a rectangular shape, a rhombic shape, or an ellipsoidal shape.

The connector 240 includes a band or wire-typed band which is substantially shaped like letter "U" and is integrated with or detachably connected to the end part (that is, the end opposite to the side on which the suspender 210 is worn) of the main body 200. The connector 240 made of a is worn on the rear side of a user's neck N such that the inner circumference part R of the connector 240 is stably placed around the rear side of a user's neck N. Therefore, the connector 240 can be easily and stably placed around the neck.

The connector 240 shaped like a band interconnects a pair of body assemblies, which include a left body assembly and a right body assembly, and each of which is configured by the main body 200, the suspender 210, and the unit body 220. The connector 240 is designed to be provided between the two main bodies 200 while having a wearing inclination angle a with respect to the lengthwise longitudinal axis C of the main body 200 wherein the wearing inclination angle is determined through experiments. The inner circumferential part R of the connector 240 has a substantially semi-circular sectional shape and comes into elastic contact with the rear middle and lower portions of the neck N of the user when the headset assembly is worn on the neck.

The inner circumferential part R of the connector 240 is designed to have a diameter slightly larger than normal neck circumference as described above, so as to provide an extra space M between the inner circumference part R of the connector 240 and the neck N of the user.

The extra space M allows users P having various neck circumference sizes to use a connector 240 having a fixed single inner diameter and thus minimizes the possibility of replacement of the connector 240 according to the users.

In spite of the extra space M of the connector 240, the user's neck N does not contact a headrest even when the user P leans his or her head against the headrest, so as to prevent the user from feeling a sense of foreign body or pressure applied to the user's head H.

In the above structure, if the length L of the main body 200 in the direction of the longitudinal axis C is not sufficiently long, the connection point at which the connector 240 starts to extend from the end of the main body 200 is located at an upper part of the head H of the user P. Therefore, in order to enable the connector 240 to be located around the neck N, the wearing inclination angle a should be a considerably acute angle. Then, the contact between the connector and the neck N of the user P is degraded, the user's wearing sense is also deteriorated, and it is difficult to achieve a stable contact therebetween.

The longitudinal length L of the main body 200 and the wearing inclination angle a with respect to the longitudinal axis C may be determined through experiments and on the basis of statistical data, and various data can be variously selected according to circumstances and locations where the present disclosure is applied.

The technical idea of a headset assembly using bone conduction according to the present disclosure is advantageous in view of the followings.

Statistically, the distance k between the upper end e of an ear E of a user P, on which the suspender is to be worn, and the upper end f of the spine, which is the upper end of the neck N, does not show a big difference between oriental people and western people.

Therefore, a headset assembly using bone conduction according to the present disclosure, having a main body 200 elongated in the direction of the longitudinal axis C and a connector extending with a wearing inclination angle a from the end of the main body 200, can be applied to nearly all fields with extremely small exceptions and thus can be used by nearly all types of users. Accordingly, the headset assembly according to the present disclosure can be sold or exported to nearly all types of users P regardless of physical properties of the users, without local limitations, and with a single size connector 240.

As described above, the connector 240 connected with a wearing inclination angle a to the end of the main body 200 shaped like a length liner having a relatively longer length in the direction of the longitudinal axis C, can be applied to various circumference sizes of necks N of users P, can be stably placed on a neck N, and can be worn around the neck N of a long-haired woman regardless of the volume of her hair. Therefore, the headset assembly according to the present disclosure has a remarkably reduced limit in the range of its users.

In addition to the above construction, the vibration plate unit 233 of the bone conduction unit 230 may be configured by either a separate electrode body or a conductive body (not shown) insulated from an electric terminal for a sound signal.

By transmitting a controlled TENS signal as disclosed in the registered patent belonging to the present inventor, a headset assembly using bone conduction according to the present disclosure enables a user to perform sound listening and TENS treatment simultaneously or selectively.

REFERENCE NUMERALS

200: main body
230: bone conduction unit
220: unit body

What is claimed is:
1. A bone conduction-using headset assembly for conducting a sound signal to a human body through mechanical vibration, the headset assembly comprising:
a pair of main bodies, each of which comprises a reception box for receiving an electric member, extends downward at a rear side of an ear of a user, and has a length longer in a longitudinal direction thereof than in a transverse direction thereof;

a pair of unit bodies separated and spaced from the main bodies, each of the unit bodies comprising a reception box that contains a bone conduction unit, wherein the bone conduction unit comprises a vibration plate unit and an electrode member, and an electric signal for transcutaneous electrical nerve stimulation (TENS) is applied from a control device, so as to enable the user to perform sound listening and TENS treatment simultaneously or selectively;

a pair of suspenders for electrically and mechanically connecting the main bodies and the unit bodies, respectively, each of the suspenders being held and suspended on the ear of the user and having a shape of letter "U"; and a connector connected to the main bodies to be worn on a head of the user, the connector being configured by a band, wherein the connector extends from ends of the main bodies toward the rear side of a neck of the user at a wearing inclination angle a with respect to a longitudinal axis of the main body, so that an inner circumference part of the connector is located around the rear side of the neck of the user when the headset assembly is worn on the user, wherein the inner circumferential part of the connector has a diameter slightly larger than a statistical standard neck circumference, so as to provide an extra space between the inner circumference part of the connector and the neck of the user, and wherein each of the main bodies extends downward at the rear side of the ear of the user by a length suitable to allow the connector fixed to the ends of the main bodies to be placed around the neck of the user.

* * * * *